(12) United States Patent
Rode et al.

(10) Patent No.: US 12,384,755 B2
(45) Date of Patent: Aug. 12, 2025

(54) PROCESS FOR THE SYNTHESIS OF FURANDICARBOXYLIC ACID

(71) Applicant: COUNCIL OF SCIENTIFIC AND INDUSTRIAL RESEARCH, New Delhi (IN)

(72) Inventors: Chandrashekhar Vasant Rode, Maharashtra (IN); Mahesh Shantappa Dharne, Maharashtra (IN); Roopa Dhanraj Parate, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 564 days.

(21) Appl. No.: 17/785,357

(22) PCT Filed: Dec. 18, 2020

(86) PCT No.: PCT/IN2020/051033
§ 371 (c)(1),
(2) Date: Jun. 14, 2022

(87) PCT Pub. No.: WO2021/124354
PCT Pub. Date: Jun. 24, 2021

(65) Prior Publication Data
US 2023/0013641 A1    Jan. 19, 2023

(30) Foreign Application Priority Data
Dec. 19, 2019 (IN) .............................. 201911052885

(51) Int. Cl.
*C07D 307/68* (2006.01)
(52) U.S. Cl.
CPC .................. *C07D 307/68* (2013.01)

(58) Field of Classification Search
CPC .............. C07D 307/68; C12R 2001/01; C12R 2001/22; C12N 1/205; C12P 7/44; C12P 17/04
USPC ........................................................ 549/429
See application file for complete search history.

(56) References Cited

FOREIGN PATENT DOCUMENTS

| CN | 105418561 A | 3/2016 |
| CN | 107739354 A | 2/2018 |
| CN | 108484545 A | 9/2018 |
| CN | 109574962 A | 4/2019 |

OTHER PUBLICATIONS

Tang et al., "Chemoselective hydrogenation of biomass derived 5-hydroxymethylfurfural to diols: Key intermediates for sustainable chemicals, materials and fuels", Renewable and Sustainable Energy Reviews 77: 287-296 (2017).

(Continued)

*Primary Examiner* — Taylor V Oh
(74) *Attorney, Agent, or Firm* — Merchant & Gould P.C.; Daniel R. Evans (57) ABSTRACT

The present invention provides a process for the synthesis of Furandicarboxylic acid (FDCA) comprising heating a mixture of fructose, aqueous NaCl or KCl, solvent, methyl isobutyl ketone (MIBK) and a catalyst at a temperature in the range of 150 to 200° C. in a sealed vessel for a time period in the range of 2 to 5 hours to yield crude 5-(hydroxymethyl)furfural (5-HMF). The crude 5-HMF further reacts with a biocatalyst at a temperature in a range of 20 to 50° C. for a period at a range of 24 to 96 hours to yield FDCA, wherein the conversion of 5-HMF to FDCA is in the range of 90 to 100%.

6 Claims, 4 Drawing Sheets

(56) References Cited

OTHER PUBLICATIONS

Hossain et al., "Metabolic Engineering of Raoultella ornithinolytica BF60 for Production of 2,5-Furandicarboxylic Acid from 5-hydroxymethylfurfural", Applied and Environmental Microbiology 83(1): e02312-02316 (2016).

PROCESS FOR THE SYNTHESIS OF FURANDICARBOXYLIC ACID

This application is a National Stage Application of PCT/IN2020/051033, filed Dec. 18, 2020, which claims benefit of priority to application No. 201911052885, filed Dec. 19, 2019, in India, and which applications are incorporated herein by reference. To the extent appropriate, a claim of priority is made to each of the above disclosed applications.

FIELD OF THE INVENTION

The present invention relates to a process for the synthesis of Furandicarboxylic acid. More particularly, the present invention relates to a process for selective conversion of 5-hydroxymethylfurfural (5-HMF) to Furandicarboxylic acid (FDCA).

BACKGROUND OF THE INVENTION

Currently, an efficient approach to transform biomass derived carbohydrates into value-added chemicals is a high priority. Oxidation of 5-(Hydroxymethyl)furfural (5-HMF) gives 2,5-Furandicarboxylic acid (FDCA) and 2,5-diformylfuran (DFF) which are considered as green alternatives for current terephthalate (PET) polymeric plastics. FDCA is considered as one of the top 12 platform chemicals, thus highly efficient sustainable and cost-effective process for large scale is a major challenge. 5-(Hydroxymethyl)furfural (5-HMF) is a promising building block derived from the dehydration of $C_6$ sugars (e.g. glucose and fructose).

Currently PET is synthesized by terephthalic acid which is obtained from petroleum derivative p-xylene. The presence of corrosive acetic acid which leads to formation of several greenhouse gases like carbon dioxide and carbon monoxide. Other oxidation product of huge significance includes 5-formylfuran-2-carboxylic acid (FFCA) a cross-linked polymer and 5-hydroxymethyl-2-furan carboxylic acid (HMFCA) also serve as a monomer for various polymer and also has the activity for antimicrobial and antitumor specifically act as an interleukin for blood cancer.

Xing Tang et al. [Chemoselective hydrogenation of biomass derived 5-hydroxymethylfurfural to diols: Key intermediates for sustainable chemicals, materials and fuels, *Renewable and Sustainable Energy Reviews*, 2017, 77, pp 287-296] reported the advances in the selective hydrogenation of 5-HMF into these diols in terms of the diversity of hydrogen sources, mainly including molecular $H_2$, alcohols, formic acid and water, over homogeneous or heterogeneous catalysts. Assessment of the relative merits of different hydrogen sources for the hydrogenation of 5-HMF is performed as well. Gazi Sakir Hossain et al [Metabolic Engineering of *Raoultella ornithinolytica* BF60 for Production of 2,5-Furandicarboxylic Acid from 5-hydroxymethylfurfural, *Applied and Environmental Microbiology*, 2016, 02312-16] reported an environmentally friendly process for the production of FDCA from 5-hydroxymethyl furfural (5-HMF) using a newly isolated strain, *Raoultella ornithinolytica* BF60. *R. ornithinolytica* BF60 was identified by screening and was isolated. Its maximal FDCA titer was 7.9 g/liter, and the maximal molar conversion ratio of 5-HMF to FDCA was 51.0% (mol/mol) under optimal conditions (100 mM 5-HMF, 45 g/liter whole-cell biocatalyst, 30° C., and 50 mM phosphate buffer [pH 8.0]). Next, dcaD, encoding dicarboxylic acid decarboxylase, was mutated to block FDCA degradation to furoic acid, thus increasing FDCA production to 9.2 g/liter. Subsequently, aldR, encoding aldehyde reductase, was mutated to prevent the catabolism of 5-HMF to HMF alcohol, further increasing the FDCA titer, to 11.3 g/liter. Finally, the gene encoding aldehyde dehydrogenase was over expressed. The FDCA titer increased to 13.9 g/liter, 1.7 times that of the wild-type strain, and the molar conversion ratio increased to 89.0%.

The major hurdle indeed is the isolation and purification of 5-HMF which is proved to be most troublesome process since, 5-HMF is not easy to be extracted from aqueous phase as the distribution coefficient between the organic and the aqueous phase is not favorable. However, this problem can be overcome by the use of organic solvents such as MIBK (methyl isobutyl ketone).

In the prior arts, 5-HMF was used commercially and also the strains were also metabolically engineered to produce FDCA for higher conversion. So there is need to develop a microbial catalyzed process for selective conversion of 5-hydroxymethylfurfural (5-HMF) to Furandicarboxylic acid (FDCA) with higher conversion and also without metabolically engineered strains.

OBJECTIVES OF THE INVENTION

The main objective of the present invention is to provide a process for synthesis of Furandicarboxylic acid (FDCA).

Another objective of the present invention is to provide a process for selective conversion of 5-hydroxymethylfurfural (5-HMF) to Furandicarboxylic acid (FDCA).

SUMMARY OF THE INVENTION

In an aspect of the present invention, there is provided a process for the synthesis of Furandicarboxylic acid (FDCA) comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield 5-hydroxymethylfurfural 5-HMF; b) suspending a biocatalyst in saline followed by addition of 5-HMF of step (a) and followed by heating at a temperature in a range of 20 to 50° C. for a time period at a range of 24 to 96 hours to yield Furandicarboxylic acid (FDCA), wherein the conversion of 5-HMF to FDCA is in the range of 90 to 100%.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only". Throughout this specification, unless the context requires otherwise the word "comprise", and variations such as "comprises" and "comprising", will be understood to imply the inclusion of a stated element or step or group of element or steps but not the exclusion of any other element or step or group of element or steps.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature in the range of 20 to 50° C. should be interpreted to include not only the explicitly recited limits of about 20° C. to 50° C. but also to include sub-ranges, such as 21 to 49° C., 25° C. to 45° C. and so forth, as well as individual amounts, within the specified ranges, such as 28.2° C., and 30.5° C.

The term "crude HMF" is defined as 5-HMF synthesized from biomass (fructose). In the present invention, the crude HMF obtained from biomass (fructose) is found to have 90 to 99% purity. In the present invention the terms "crude HMF", 'crude 5-HMF" may be used interchangeably.

The term "biocatalyst" refers to a natural substance such as enzyme, hormone or microorganisms which can activates or accelerates a chemical or biochemical reaction. In the present invention, the biocatalyst refers to the bacterial strains *Klebsiella pneumoniae*, *Klebsiella oxytoca*, *Enterobacter aerogenes* and *Enterobacter cloacae*

Bacterial strains *Klebsiella pneumoniae* NCIM 5215, *Klebsiella oxytoca* NCIM 2694, *Enterobacter aerogenes* NCIM 2695 and *Enterobacter cloacae* NCIM 2562 were obtained from National Collection of Industrial Microorganisms (NCIM) repository, Pune, India. The accession numbers assigned by National Center for Microbial Resource, Pune, India are as follows:

| | |
|---|---|
| *Klebsiella pneumoniae* NCIM 5215 | MCC0143 |
| *Klebsiella oxytoca* NCIM 2694 | MCC0144 |
| *Enterobacter aerogenes* NCIM 2695 | MCC0135 |
| *Enterobacter cloacae* NCIM 2562 | MCC0136 |

Fructose was commercially obtained from Thomas Baker (99.4% purity).

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent molecules, compositions, and methods are clearly within the scope of the disclosure, as described herein.

In an embodiment of the present invention there is provided a process for the synthesis of 5-HMF comprising the steps of a) heating a mixture of fructose, aqueous NaCl or KCl, a solvent, methyl isobutyl ketone (MIBK) and a catalyst at a temperature in the range of 150 to 200° C. in a sealed vessel for a time period in the range of 2 to 5 hours to yield crude 5-HMF.

In an embodiment of the present invention, there is provided a process for the synthesis of Furandicarboxylic acid comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield crude 5-hydroxymethylfurfural (5-HMF); b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA) and wherein the conversion of 5-HMF to FDCA is in the range of 90 to 100%.

In an embodiment of the present invention, there is provided a process for selective conversion of crude 5-hydroxymethylfurfural (5-HMF) to Furandicarboxylic acid (FDCA) comprising the steps of: a) heating a mixture of fructose, aqueous NaCl or KCl, solvent, methyl isobutyl ketone (MIBK) and a catalyst at a temperature in a range of 150 to 200° C. in a sealed vessel for a time period in a range of 2 to 5 hours to yield crude 5-HMF; b) suspending a biocatalyst in saline followed by addition of crude 5-HMF of step (a) in a reaction tube and placing the reaction tube in orbital shaker at a temperature in a range of 20 to 50° C. and 100 to 200 rpm for a period at a range of 24 to 96 hours to yield Furandicarboxylic acid (FDCA), wherein the conversion of 5-HMF to FDCA is in the range of 90 to 100%.

In an embodiment of the present invention, there is provided a process for the synthesis of Furandicarboxylic acid as disclosed herein, wherein said catalyst of step (a) is an acid.

In an embodiment of the present invention, there is provided a process for the synthesis of Furandicarboxylic acid comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield crude 5-hydroxymethylfurfural (5-HMF);

b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA) and wherein the conversion of 5-HMF to FDCA is in the range of 90 to 100% and wherein said catalyst of step (a) is an acid.

In an embodiment of the present invention, there is provided a process for the synthesis of Furandicarboxylic acid as disclosed herein, wherein the catalyst of step (a) is selected from acid wherein the acid is homogeneous or heterogeneous.

In an embodiment of the present invention, there is provided a process for the synthesis of Furandicarboxylic acid as disclosed herein, wherein the homogeneous acid is capable of providing proton and the homogeneous acid is selected from $H_2SO_4$, HCl or $HNO_3$.

In an embodiment of the present invention, there is provided a process for the synthesis of Furandicarboxylic acid as disclosed herein, wherein the heterogeneous acid is selected from Amberlyst-15, $SO_4^{2-}/ZrO_2—Al_2O_3$, $GeCCl_4$ and $CrCl_2$.

In an embodiment of the present invention, there is provided a process for the synthesis of Furandicarboxylic acid as disclosed herein, wherein the ratio of fructose to catalyst is 10:1.

In an embodiment of the present invention, there is provided a process for the synthesis of Furandicarboxylic acid comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield crude 5-hydroxymethylfurfural (5-HMF); b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA) and wherein the conversion of 5-HMF to FDCA is in the range of 90 to 100% and wherein the ratio of fructose to catalyst is 10:1.

In an embodiment of the present invention, there is provided a process for the synthesis of Furandicarboxylic acid as disclosed herein, wherein the solvent of step (a) is selected from dimethyl sulfoxide, N,N-dimethylformamide and N,N-dimethylacetamide.

In an embodiment of the present invention, there is provided a process for the synthesis of Furandicarboxylic acid comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield crude 5-hydroxymethylfurfural (5-HMF); b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA) and wherein the conversion of 5-HMF to FDCA is in the range of 90 to 100% and wherein the solvent of step (a) is selected from dimethyl sulfoxide, N,N-dimethylformamide and N,N-dimethylacetamide.

In an embodiment of the present invention, there is provided a process for the synthesis of Furandicarboxylic acid as disclosed herein, wherein the biocatalyst of step (b) is selected from *Klebsiella pneumoniae, Klebsiella oxytoca, Enterobacter aerogenes* and *Enterobacter cloacae*.

In an embodiment of the present invention, there is provided a process for the synthesis of Furandicarboxylic acid comprising the steps of a) heating a mixture of fructose, aqueous NaCl or KCl, a solvent, methyl isobutyl ketone (MIBK) and a catalyst at a temperature in a range of 150 to 200° C. in a sealed vessel for a time period in a range of 2 to 5 hours to yield crude 5-hydroxymethylfurfural (5-HMF); b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA) and wherein the conversion of 5-HMF to FDCA is in the range of 90 to 100% and wherein said biocatalyst of step (b) is selected from *Klebsiella pneumoniae, Klebsiella oxytoca, Enterobacter aerogenes* and *Enterobacter cloacae*.

In an embodiment of the present invention, there is provided a process for the synthesis of Furandicarboxylic acid as disclosed herein, wherein 5-HMF is used in the range of 2000-5000 mg/L.

In an embodiment of the present invention, there is provided a process for the synthesis of Furandicarboxylic acid as disclosed herein, wherein the cell culture is used in the range of 0.5 g to 1.5 g.

In an embodiment of the present invention, there is provided a process for the synthesis of Furandicarboxylic acid comprising the steps of a) heating a mixture of fructose, aqueous NaCl or KCl, a solvent selected from dimethyl sulfoxide, N,N-dimethylformamide or N,N-dimethylacetamide, methyl isobutyl ketone (MIBK) and an acid at a temperature in a range of 150 to 200° C. in a sealed vessel for a time period in a range of 2 to 5 hours to yield crude 5-hydroxymethylfurfural (5-HMF); b) suspending a biocatalyst selected from *Klebsiella pneumoniae, Klebsiella oxytoca, Enterobacter aerogenes* and *Enterobacter cloacae* in saline followed by addition of crude 5-HMF of step (a) and followed by heating at a temperature in a range of 20 to 50° C. for a time period at a range of 24 to 96 hours to yield Furandicarboxylic acid (FDCA), wherein the acid is homogenous acid or heterogenous acid, the ratio of fructose to the catalyst is 10:1 and the conversion of 5-HMF to FDCA is in the range of 90 to 100%.

In an embodiment of the present invention, there is provided a process for the synthesis of Furandicarboxylic acid as disclosed herein, wherein 5-HMF and FDCA are characterized by Ultra High Performance Liquid Chromatography (UHPLC).

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

Examples

The disclosure will now be illustrated with the working examples, which is intended to illustrate the working of disclosure and not intended to take restrictively to imply any limitations on the scope of the present disclosure. Unless defined otherwise, all technical and scientific terms used herein have the same meaning as commonly understood to one ordinary person skilled in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Abbreviation

Figure 1:
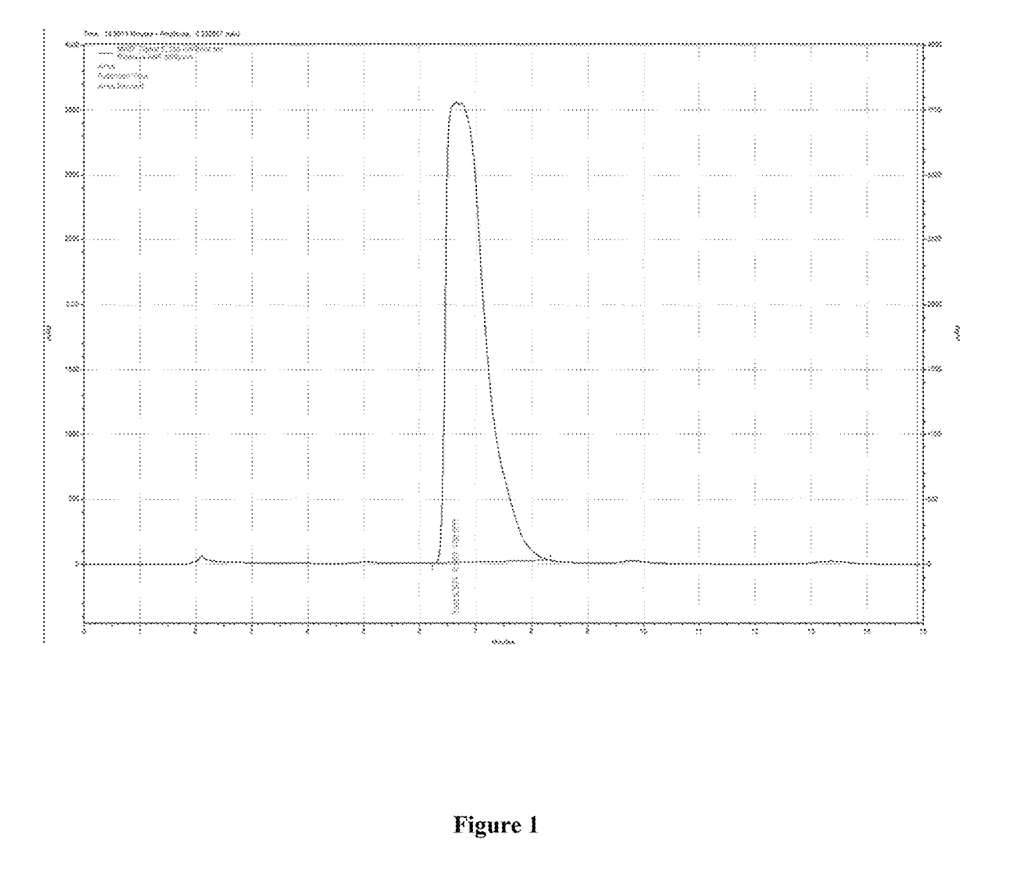
FIG. 1 depicts the chromatogram showing peak of crude 5-HMF (3000 ppm), in accordance with an implementation of the present invention.
Figure 2:
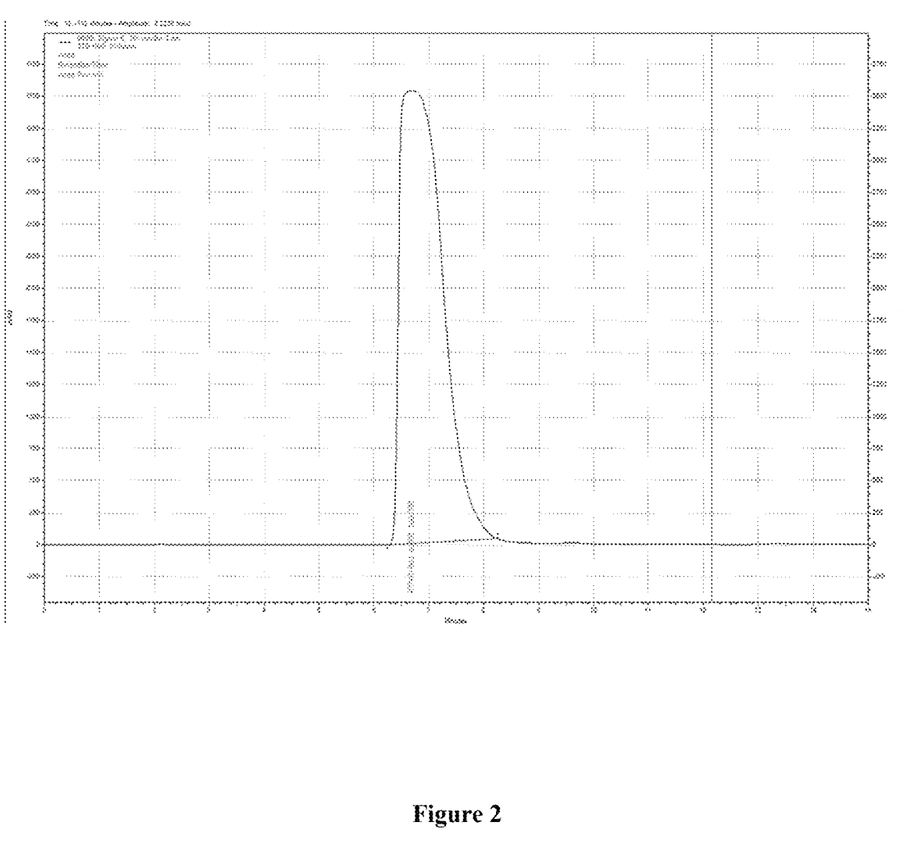
FIG. 2 depicts the chromatogram showing peak of pure 5-HMF, in accordance with an implementation of the present invention.
Figure 3:
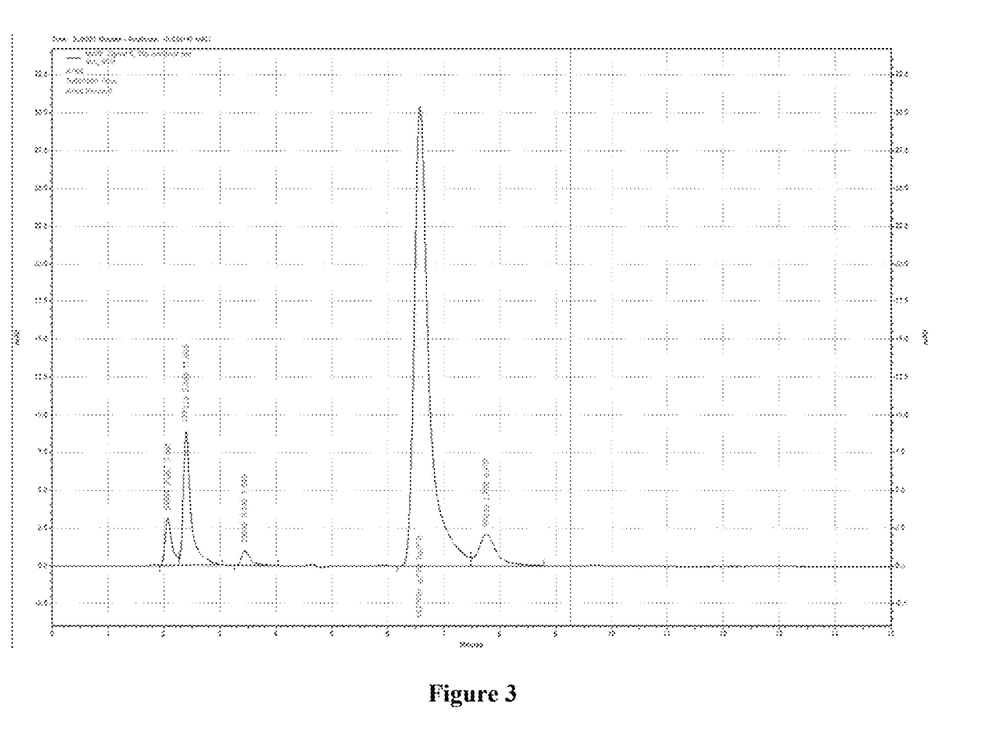
FIG. 3 depicts the chromatogram showing peaks of substrate and products, in accordance with an implementation of the present invention.

HMF/5-HMF: 5-Hydroxymethylfurfural
FDCA: Furandicarboxylic acid
NaCl: Sodium Chloride
KCl: Potassium chloride
DMSO: Dimethyl sulfoxide
MIBK: Methyl isobutyl ketone
HMFCA: Hydroxymethyl-2-furancarboxylic acid
FFCA: Formyl-2-furancarboxylic Acid
DFF: Diformylfuran $H_2SO_4$: Sulfuric acid
HCl: Hydrochloric acid
$HNO_3$: Nitric acid
$CrCl_2$: Chromous chloride
UHPLC: Ultra High Performance Liquid Chromatography
$SO_4^{2-}/ZrO_2$—$Al_2O_3$: Sulphated-Zirconia-Alumina
$GeCl_4$: Germanium tetrachloride FIG. 1 depicts chromatogram showing peak of crude HMF (3000 ppm) at retention time 6.6. FIG. 2 depicts chromatogram showing peak of pure HMF at retention time 6.6. FIG. 3 depicts chromatogram showing peaks of substrate (5-HMF) at retention time 6.6 and products (FDCA) at retention time 2.1. Table 1 shows results of Ultra High Performance Liquid Chromatography (UHPLC) of substrate and products.

TABLE 1

| Retention Time | Molecule |
|---|---|
| 2.1 | FDCA |
| 2.3 | FFCA |
| 3.4 | HMFCA |
| 5.0 | Furoic acid |
| 6.6 | HMF |
| 7.7 | DFF |

Utilizing 5-HMF as the sole substrate without any additional nutrient requirement, the microorganism converted crude 5-HMF to various products (FDCA, HMFCA, FFCA and others) as shown in table 2. Highest conversion at the end of 96 h was shown by *Klebsiella oxytoca* MCC0144 with highest selectivity towards FDCA (66%) 1971 mg/L and 34% of HMFCA with 1019 mg/L yield. *Enterobacter cloacae* MCC0136 showed highest selectivity towards FFCA i.e. 73%, 1916 mg/L yield. However *Klebsiella pneumoniae* MCC0143 and *Enterobacter aerogenes* MCC0135 showed similar distribution for FDCA and HMFCA with 81% and 98% crude HMF conversion.

Figure 4:
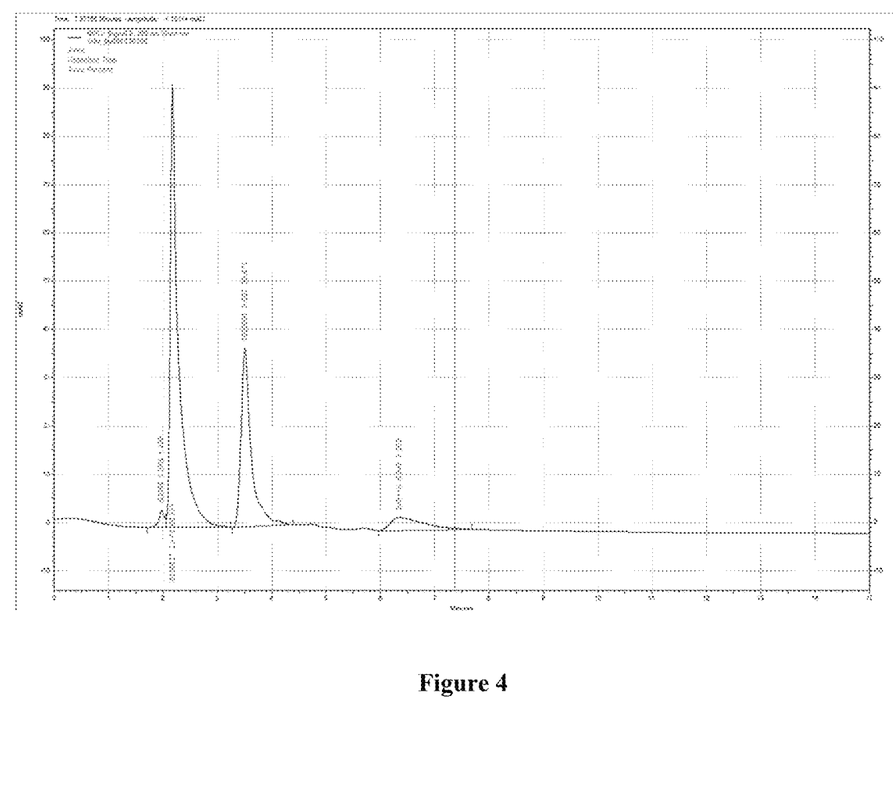
FIG. 4 depicts the chromatogram for *Klebsiella oxytoca* NCIM 2694_dry crude, in accordance with an implementation of the present invention.

FIG. 4 shows chromatogram peaks of products obtained after rota evaporation studies (43° C., 225 mbar), confirming the presence of FDCA and HMFCA through UHPLC analysis. UHPLC analysis shows retention time of FDCA and HMFCA are 2.1 and 3.4 respectively.

This process provides high selectivity for a particular product and almost complete utilization of crude 5-HMF is observed. No addition of further nutrients during bioconversion will help in decreasing the cost of the process at larger scale. Table 2 shows conversion of crude 5-HMF by microorganisms into products[a]

TABLE 2

| Sr. No. | Strain (NCIM) | Conversion (%)_96 h | Products (mg/L)/Selectivity (%) | | | |
|---|---|---|---|---|---|---|
| | | | FDCA | HMFCA | FFCA | *Others |
| 1 | *Klebsiella pneumoniae* 5215 | 81 | 1033 mg/L 43% | 1139 mg/L 46% | — | 257 mg/L 11% |
| 2 | *Enterobacter aerogenes* 2695 | 98 | 978 mg/L 33% | 1738 mg/L 58% | — | 236 mg/L 9% |
| 3 | *Enterobacter cloacae* 2562 | 87 | 322 mg/L 12% | 75 mg/L 3% | 1916 mg/L 73% | 300 mg/L 12% |
| 4 | *Klebsiella oxytoca* 2694 | 99 | 1971 mg/L 66% | 1019 mg/L 34% | — | — |

[a] Reaction conditions: pH 7, 30° C., 1 g cells, 3000 mg/L 5-HMF, 150 rpm and 96 h.
*Others refers to the by-products formed which include DFF [diformylfuran].

Materials:

Crude 5-HMF was prepared from fructose as listed in example 1. Chemicals such as FDCA and standard 5-HMF were purchased from Sigma-Aldrich (USA) and HMFCA was obtained from Alfa Aesar whereas FFCA, DFF was obtained from TCI chemicals. Fructose was commercially obtained from Thomas Baker (99.4% purity).

Example 1: Procedure for Production of Crude 5-HMF from Fructose

A mixture of fructose (50 g), 10% aqueous NaCl solution (150 mL), DMSO (50 mL), MIBK (800 mL) and $H_2SO_4$ (20 mol %) or Amberlyst-15 (10 g, 20 wt %) were heated at 170° C. in a sealed vessel for 3 h. The reaction mixture was then filtered and the filtrate was neutralized and then aqueous layer was extracted with ethyl acetate. Subsequently, combined organic phase (including MIBK and ethyl acetate) was dried over anhydrous $Na_2SO_4$ (50 g) and evaporated to obtain brown oil of crude 5-HMF of about 20 g. FIG. 1 shows the chromatogram of the 5-HMF (retention time 6.6) and this indicates that crude 5-HMF is 98.40% purity as compared to standard 5-HMF (retention time 6.6) (FIG. 2).

In presence of mineral acid (conc. $H_2SO_4$, 20 mol %), fructose was consumed completely in just 1 h with total 44% yield of 5-HMF (Table 3, entry 1). In presence of Amberlyst-15, fructose was consumed up to 98% with 51% isolated yield of 5-HMF (Table 3, entry 2). On the other hand, with AmberlyteIR-120, higher yield (58%) of 5-HMF was achieved (Table 3, entry 3). Over Zr-Mont, a 49% yield of 5-HMF was achieved (Table 3, entry 4).

TABLE 3

Dehydration of fructose over different acid catalysts in biphasic solvent system [a]

| Entry | Catalyst | Loading | Conv. [%] | HMF, Isolated yield [%] |
|---|---|---|---|---|
| 1[b] | H₂SO₄ | 20 mol % | 99 | 4415 |
| 2 | Amberlyst-15 | 10 g | 98 | 51 |
| 3 | Amberlyte IR-120 | 10 g | 99 | 58 |
| 4 | Zr-Mont | 10 g | 98 | 49 |

[a] Reaction conditions: Fructose (50 g), DMSO (50 mL), H2O-NaCl (150 mL), MIBK (800 mL), catalyst, 170° C., 12 h.
[b]Reaction time, 3 h. Conversion of fructose and yield of HMF were determined using UHPLC. For entry 2, 3 and 4 reaction time is 12 h for maximum conversion, whereas entry1 reaction time is 3 h for maximum conversion.

Example 2: Microorganisms and Growth Conditions

Bacterial strains *Klebsiella pneumoniae* NCIM 5215, *Klebsiella oxytoca* NCIM 2694, *Enterobacter aerogenes* NCIM 2695 and *Enterobacter cloacae* NCIM 2562 were obtained from National Collection of Industrial Microorganisms (NCIM) repository, Pune, India. The accession numbers assigned by National Center for Microbial Resource, Pune, India are as follows:

| | |
|---|---|
| *Klebsiella pneumoniae* NCIM 5215 | MCC0143 |
| *Klebsiella oxytoca* NCIM 2694 | MCC0144 |
| *Enterobacter aerogenes* NCIM 2695 | MCC0135 |
| *Enterobacter cloacae* NCIM 2562 | MCC0136 |

Pure cultures were inoculated for making seed culture in 10 mL of Nutrient Broth (HiMedia Laboratories, India) and incubated in orbital shaker at 30° C., 150 rpm for 24 h.

Example 3: Bioconversion Using Direct Crude 5-HMF by Using *Klebsiella pneumoniae*

The culture of *Klebsiella pneumoniae* was inoculated for making seed culture in 10 mL of Nutrient Broth (HiMedia Laboratories, India) and incubated in orbital shaker at 30° C., 150 rpm for 24 h. The seed cultures of *Klebsiella pneumoniae*, was centrifuged at 10,000 rpm for 10 min at 4° C., pellets were suspended in saline (0.85% NaCl), vortexed for 10 sec (repeated twice) and wet weight of pellet was noted. The pellet (1 g) was then suspended in 9.58 mL saline and 0.42 mL of crude 5-HMF was added to achieve 3000 mg/L final concentration in 50 mL reaction tubes (final pH 7.0). The tubes were placed in orbital shaker at 30° C., 150 rpm. Control reaction tubes contained only crude HMF and saline. Experiments were performed in replicates. (Refer table 2).

Example 4: Bioconversion Using Direct Crude 5-HMF by Using *Klebsiella oxytoca*

The culture of *Klebsiella oxytoca* was inoculated for making seed culture in 10 mL of Nutrient Broth (HiMedia Laboratories, India) and incubated in orbital shaker at 30° C., 150 rpm for 24 h. The seed cultures of *Klebsiella oxytoca*, was centrifuged at 10,000 rpm for 10 min at 4° C., pellets were suspended in saline (0.85% NaCl), vortexed for 10 sec (repeated twice) and wet weight of pellet was noted. The pellet (1 g) was then suspended in 9.58 mL saline and 0.42 mL of crude 5-HMF was added to achieve 3000 mg/L final concentration in 50 mL reaction tubes (final pH 7.0). The tubes were placed in orbital shaker at 30° C., 150 rpm. Control reaction tubes contained only crude HMF and saline. Experiments were performed in replicates. (Refer table 2)

Example 5: Bioconversion Using Direct Crude 5-HMF by Using *Enterobacter aerogenes*

The culture of *Enterobacter aerogenes* was inoculated for making seed culture in 10 mL of Nutrient Broth (HiMedia Laboratories, India) and incubated in orbital shaker at 30° C., 150 rpm for 24 h. The seed cultures of *Enterobacter aerogenes*, was centrifuged at 10,000 rpm for 10 min at 4° C., pellets were suspended in saline (0.85% NaCl), vortexed for 10 sec (repeated twice) and wet weight of pellet was noted. The pellet (1 g) was then suspended in 9.58 mL saline and 0.42 mL of crude 5-HMF was added to achieve 3000 mg/L final concentration in 50 mL reaction tubes (final pH 7.0). The tubes were placed in orbital shaker at 30° C., 150 rpm. Control reaction tubes contained only crude HMF and saline. Experiments were performed in replicates. (Refer table 2)

Example 6: Bioconversion Using Direct Crude 5-HMF by Using *Enterobacter cloacae*

The culture of *Enterobacter cloacae* was inoculated for making seed culture in 10 mL of Nutrient Broth (HiMedia Laboratories, India) and incubated in orbital shaker at 30° C., 150 rpm for 24 h. The seed cultures of *Enterobacter cloacae* was centrifuged at 10,000 rpm for 10 min at 4° C., pellets were suspended in saline (0.85% NaCl), vortexed for 10 sec (repeated twice) and wet weight of pellet was noted. The pellet (1 g) was then suspended in 9.58 mL saline and 0.42 mL of crude 5-HMF was added to achieve 3000 mg/L final concentration in 50 mL reaction tubes (final pH 7.0). The tubes were placed in orbital shaker at 30° C., 150 rpm. Control reaction tubes contained only crude HMF and saline. Experiments were performed in replicates. (Refer table 2)

Example 7: Analytical Methods

About 1.0 mL of reaction sample was withdrawn at the end of 24 h and 48 h each, centrifuged at 10,000 rpm for 10 min at 4° C. and filtered through a 0.22 μm filter (Millipore, USA). Clear supernatant was used for the determination of products (FDCA, HMFCA, FFCA, DFF, furoic acid) and analysed by Ultra High Performance Liquid Chromatography (Model-Agilent Technologies 1260 infinity series) equipped with an autosampler, UV detector (280 nm, 4 bw) on a HiPlex column (45° C.) using 85% (0.1%) water (Acetic acid): 15% Acetonitrile as the mobile phase. FDCA, HMFCA, FFCA, DFF and furoic acid standards were also analysed by UHPLC. (Refer Table 1).

Advantages of the Invention

The present invention provides an efficient process for the synthesis of FDCA from a biomass (fructose) in the presence of a catalyst via conversion of 5-HMF to FDCA. The process of the present invention provides high selectivity for a particular product and almost complete utilization of crude 5-HMF. No addition of further nutrients during bioconversion, helps in decreasing the cost of the process at larger scale. The process of the present disclosure provides a sustainable and greener approach by combining chemocatalytic and biocatalytic process. The present disclosure provides a process for direct conversion of fructose into FDCA and the FDCA is used for preparation of polyurethane. FDCA is a strong alternate of current monomer of PET plastic. Microorganisms could carry out the conversion of crude 5-HMF to FDCA without extra supplementation of nutrients. The present invention overcomes the shortcoming of prior art which uses commercial 5-HMF whereas in the present invention biomass (fructose) derived 5-HMF is used. The strains are also metabolically engineered to produce FDCA for higher conversion (51% to 89%), however in the present invention strains are not metabolically engineered giving higher conversion as much as 99% FDCA.

We claim:

1. A process for the synthesis of Furandicarboxylic acid comprising the steps of:
   a) heating a mixture of fructose, aqueous NaCl or KCl, a solvent, methyl isobutyl ketone (MIBK) and an acid catalyst at a temperature in a range of 150 to 200° C. in a sealed vessel for a time period in a range of 2 to 5 hours to yield crude 5-hydroxymethylfurfural (5-HMF); and
   b) suspending a biocatalyst in saline followed by addition of crude 5-HMF of step (a) and followed by heating at a temperature in a range of 20 to 50° C. for a time period at a range of 24 to 96 hours to yield Furandicarboxylic acid (FDCA);
   wherein the acid catalyst in step (a) is a homogeneous acid and heterogeneous acid catalyst;
   wherein the conversion of 5-HMF to FDCA is in the range of 90 to 100%.

2. The process as claimed in claim 1, wherein said homogeneous acid catalyst is selected from the group consisting of $H_2SO_4$, HCl and $HNO_3$.

3. The process as claimed in claim 1, wherein said heterogeneous acid catalyst is selected from the group consisting of Amberlyst-15, $SO_4^{2-}/ZrO_2$—$Al_2O_3$, $GeCCl_4$ and $CrCl_2$.

4. The process as claimed in claim 1, wherein the ratio of the fructose to the acid catalyst is 10:1.

5. The process as claimed in claim 1, wherein said solvent of step (a) is selected from the group consisting of dimethyl sulfoxide, N,N-dimethylformamide and N,N-dimethylacetamide.

6. The process as claimed in claim 1, wherein said biocatalyst of step (b) is selected from the group consisting of *Klebsiella pneumoniae, Klebsiella oxytoca, Enterobacter aerogenes* and *Enterobacter cloacae*.

* * * * *